United States Patent [19]

Nielsen et al.

[11] Patent Number: 5,557,415
[45] Date of Patent: Sep. 17, 1996

[54] APPARATUS AND METHOD FOR INDUCING AND DETECTING FLUORESCENCE

[75] Inventors: Hans O. Nielsen; Jan Hansen, both of Lyngby, Denmark

[73] Assignee: Faxekalk A/S, Copenhagen, Denmark

[21] Appl. No.: 343,511

[22] PCT Filed: May 19, 1993

[86] PCT No.: PCT/DK93/00171

§ 371 Date: Dec. 21, 1994

§ 102(e) Date: Dec. 21, 1994

[87] PCT Pub. No.: WO93/23738

PCT Pub. Date: Nov. 25, 1993

[30] Foreign Application Priority Data

May 21, 1992 [DK] Denmark .................. 0669/92

[51] Int. Cl.⁶ ........................................... G01N 21/64
[52] U.S. Cl. .................. 356/417; 250/458.1; 250/461.1
[58] Field of Search ........................ 356/417, 317, 356/318; 385/12; 250/458.1, 459.1, 461.1, 461.2

[56] References Cited

U.S. PATENT DOCUMENTS

| | | |
|---|---|---|
| 2,139,797 | 12/1938 | Boerstler . |
| 2,971,429 | 2/1961 | Howerton . |
| 3,068,739 | 12/1962 | Hicks, Jr. et al. . |
| 3,510,648 | 5/1970 | Leger, Jr. . |
| 3,690,773 | 9/1972 | Malley . |
| 3,854,050 | 12/1974 | Peterson et al. . |

(List continued on next page.)

FOREIGN PATENT DOCUMENTS

| | | |
|---|---|---|
| 3026/87 | 6/1987 | Denmark . |
| 0155813 | 9/1985 | European Pat. Off. . |
| 0174722 | 3/1986 | European Pat. Off. . |
| 0214768 | 3/1987 | European Pat. Off. . |

(List continued on next page.)

OTHER PUBLICATIONS

Harrison, et al., "Fluorimetric technique for monitoring changes in the level of reduced nicotinamide nucleotides in continuous cultures of microorganisms" *Applied Microbiology*, pp. 446–450, (Mar. 1970).

Beyeler, et al., "On–Line Measurements of Culture Fluorescence: Method and Application", *European Journal of Applied Microbiology and Biotechnology*, 13: 10–14, (Apr. 1981).

(List continued on next page.)

*Primary Examiner*—F. L. Evans
*Attorney, Agent, or Firm*—Merchant, Gould, Smith, Edell, Welter & Schmidt, P.A.

[57] ABSTRACT

An apparatus and a method for inducing and detecting fluorescence in a fluid medium containing at least one fluorophore. The apparatus comprises a light emitter adapted to emit light of a wavelength capable of exciting fluorophores in the fluid medium, a light detector adapted to detect fluorescence emitted by the fluorophores excited by the exciting light, a sensor body, preferably being solid and made of quartz, having internally reflecting wall parts capable of reflecting at least light having a wavelength corresponding to the wavelength of the fluorescence and having a sensor face adapted to be exposed to the fluid medium, the sensor body being adapted to receive exciting light from the light emitter, such as via an optical fiber, and to transmit the received exciting light into the fluid medium through the sensor face, to receive, through the sensor face, fluorescence emitted by excited fluorophores in the fluid medium, and to transmit at least part of the received fluorescence to the light detector, both the light emitter and the detector being positioned in a distance from the sensor face, and the relative positioning of the light emitter, the optical detector, and the sensor face being such that the detector is able to receive light transmitted from at least a portion of that part of the sensor face which receives light from the light emitter. The apparatus is especially well suited for operation in turbid or highly turbid media such as a fermentation tank or wastewater in a wastewater purification plant.

26 Claims, 4 Drawing Sheets

U.S. PATENT DOCUMENTS

| | | |
|---|---|---|
| 3,918,812 | 11/1975 | Holm . |
| 3,941,477 | 3/1976 | Schodl . |
| 3,990,795 | 11/1976 | Parker . |
| 4,031,399 | 6/1977 | Klein et al. . |
| 4,055,768 | 10/1977 | Bromberg . |
| 4,153,675 | 5/1979 | Kleinerman . |
| 4,197,458 | 4/1980 | Perren . |
| 4,221,485 | 9/1980 | Schulze . |
| 4,293,225 | 10/1981 | Wheaton et al. . |
| 4,295,199 | 10/1981 | Curry et al. . |
| 4,447,546 | 5/1984 | Hirschfeld . |
| 4,577,110 | 3/1986 | MacBride et al. . |
| 4,644,154 | 2/1987 | Brogardh et al. . |
| 4,746,179 | 5/1988 | Dahne et al. ............................ 385/12 |
| 4,753,530 | 6/1988 | Knight et al. . |
| 5,155,046 | 10/1992 | Hui et al. ............................ 250/458.1 |
| 5,221,958 | 6/1993 | Bohnenkamp ........................ 356/417 |

FOREIGN PATENT DOCUMENTS

| | | |
|---|---|---|
| 0334533 | 9/1989 | European Pat. Off. . |
| 0335725 | 10/1989 | European Pat. Off. . |
| 0421156 | 4/1991 | European Pat. Off. . |
| 0427996 | 5/1991 | European Pat. Off. . |
| 0519622 | 12/1992 | European Pat. Off. . |
| 2205323 | 8/1973 | Germany . |
| 2534763 | 3/1976 | Germany . |
| 2842343 | 4/1980 | Germany . |
| 3020168 | 12/1981 | Germany . |
| 3409618 | 10/1984 | Germany . |
| 258471 | 7/1988 | Germany . |
| 91/15867 | 10/1991 | WIPO . |

OTHER PUBLICATIONS

Bhaumik, et al., "Stroboscopic Time–Resolved Spectroscopy", *The Review of Scientific Instruments*, vol. 36, No. 1: 37–40, (Jan. 1965).

Keirs, et al., "Phosphorimetry. A New Method of Analysis", *Analytical Chemistry*, vol. 29, No. 2: 202–209, (Feb. 1957).

Lund, "A Fiber Optics Fluorimeter for Algae Detection and Mapping", *Royal Norwegian Council for Scientific and Industrial Research, Environmental Surveillance Technology Programme, Norway*, pp. 190–194, (Jun. 1979).

Lund, "A Simple and Sensitive in situ Algea Fluorescence Sensor Based on Fiber Optics", *Royal Norwegian Council for Scientific and Industrial Research, Environmental Surveillance Technology Programme, Norway*, at pp. 1–18, (Jun. 1979).

Mayevsky, "Intracellular Oxidation–Reduction State Measured in situ by a Multichannel Fiber–Optic Surface Fluorometer", *Science*, vol. 217: 537–540, (Aug. 1982).

Mitchell, et al., "Fiber Optic Filter Fluorometer for Improved Analysis of Absorbing Solutions", *Analytical Chemistry*, vol. 48, No. 14: 2275–2277, (Dec. 1976).

Mooradian, "Application of Laser Technology to Atmospheric Monitoring", *National Bureau of Standards Special Publication 464*, at 277–286, (Nov. 1977).

Zabriskie, "Estimation of Fermentation Biomass Concentration by Measuring Culture Fluorescence", *Applied and Environmental Microbiology*, vol. 35, No. 2: 337–343, (Feb. 1978).

APPARATUS AND METHOD FOR INDUCING AND DETECTING FLUORESCENCE

BACKGROUND OF THE INVENTION

The present invention concerns a novel apparatus and method for inducing and detecting fluorescence. The apparatus is particularly useful for measuring fluorescence emitted from turbid or highly turbid fluid media, such as, e,g., fluorescence emitted from living cells in a fermentation tank or in a mixed culture in a water purification plant. Thus, the apparatus is most valuable for performing the fluorescence determinations in the method disclosed in WO90/10083 published 7 Sep. 1990, which relates to a method for controlling and/or optimising a process in which an aqueous system comprising biodegradable material, such as waste water or sewage, is subjected to biological treatment using mixed cultures of microorganisms.

U.S. Pat. No. 4,577,110 discloses an apparatus for inducing fluorescence in, and measuring fluorescence emitted from, a biological medium. The apparatus is adapted to launch, from a continuous light source, a beam of exciting light through a ring-shaped detector. The apparatus is designed so that the field of illumination of the exciting light is substantially contained within the field of view of the detector measuring the emitted fluorescence.

EP 0.047.094 discloses an apparatus for inducing and detecting fluorescence in a medium. The pulsed exciting light and the fluorescence emitted from the medium are guided to and from the measured medium by means of optical fibres.

In highly turbid media, light is not able to travel more than a few mm or even only fractions of a mm before it becomes very considerably attenuated. Therefore, fluorescence measurements in such media present severe problems, and there is a considerable demand for fluorescence measuring equipment which is able to perform measurements with a high sensitivity and over a broad dynamic range.

The present invention relates to an apparatus of a novel type which is particularly adapted for performing the inherently very difficult fluorescence measurements in highly turbid media, but which will also be advantageous for applications in less turbid or non-turbid media.

SUMMARY OF THE INVENTION

In one aspect, the invention relates to an apparatus for inducing and detecting fluorescence in a fluid medium containing at least one fluorophore, the apparatus comprising:

a light emitter adapted to emit light of a wavelength capable of exciting fluorophores in the fluid medium, a light detector adapted to detect fluorescence emitted by the fluorophores excited by the exciting light, a sensor body having internally reflecting wall parts capable of reflecting at least light having a wavelength corresponding to the wavelength of the fluorescence and having a sensor face adapted to be exposed to the fluid medium, the sensor body being adapted to receive exciting light from the light emitter, and to transmit the received exciting light into the fluid medium through the sensor face, to receive, through the sensor face, fluorescence emitted by excited fluorosphores in the fluid medium, and to transmit at least part of the received fluorescence to the light detector, both the light emitter and the detector being positioned in a distance from the sensor face, and the relative positioning of the light emitter, the optical detector, and the sensor face being such that the detector is able to receive light transmitted from at least a portion of that part of the sensor face which receives light from the light emitter.

In another aspect, the invention relates to a method for inducing and detecting fluorescence in a fluid medium containing at least one fluorophore, the method comprising:

transmitting light from a light emitter through a sensor body having internally reflecting wall parts at least capable of reflecting light having a wavelength corresponding to the wavelength of the fluorescence and through a sensor face thereof into the fluid medium, at least part of the light being of a wavelength capable of exciting the fluorophores so as to induce the emission of fluorescence, receiving, through the sensor face, fluorescence emitted by the excited fluorophores in the fluid medium, and transmitting at least part of the received fluorescence through the sensor body to a light detector adapted to detect the fluorescence emitted by the fluorophores excited by the exciting light, at least part of the fluorescence transmitted to the detector being fluorescence received through a part of the sensor face from which light from the light emitter is emitted to the fluid medium.

The fluid medium will normally be a liquid, but it may also be a mixture of a liquid and a gas, or it may be a gas with, e.g. suspended particles containing fluorophores.

The term "fluorophore" is to be understood in its accepted meaning as a substance which, when excited by absorption of electromagnetic irradiation (light), will decay to a lower energy state with emission of electromagnetic radiation having a wavelength longer than the wavelength of the exciting electromagnetic irradiation. Many important fluorescent substances may be excited with Ultra Violet light and will decay with emission of light in the visual range, but there are also substances which both absorb and emit light in the Ultra Violet region, as well as substances which both absorb and emit light in the visual region, and substances which emit in the Near Infra Red region. The apparatus according to the present invention can be used for measurements in connection with any of these types of substances, although it will be described in the following with particular emphasis on measurements on substances which absorb in the Ultra Violet region and emit visual light.

A central feature of the apparatus of the invention is the sensor body, which constitutes a particularly advantageous functional interface between on the one hand the light emitter and the light detector and on the other hand the fluid medium. One function of the sensor body is to establish such a geometrical position relation between on the one hand the liquid medium and on the other hand the light emitter and the detector that the detector is capable of receiving light from the same part of the liquid medium as has been excited by illumination with the exciting light. The importance of this relation resides in the fact that in a highly turbid medium, the available fluid volume which can be excited is represented by a layer having a thickness of only a few mm, or even only a fraction of a mm, immediately in front of the sensor face and that any part of this layer which has not received the exciting light will not contribute to the active measuring volume.

Thus, in a preferred embodiment, the relative positioning of the light emitter, the sensor face, and the optical detector is such that light emitted by the light emitter is able to directly illuminate the predominant part of the sensor face. On the other hand, as the wall parts are capable of reflecting the exciting light, any part of the emitted light which is not directly directed to the sensor face will be transmitted thereto through reflection on the walls.

In another preferred embodiment made possible through the use of the sensor body interface, the relative positioning of the light emitter, the sensor face, and the optical detector is such that the detector is able to directly receive light from a predominant proportion of the illuminated part of the sensor face. Reflection on the walls of the sensor will then further enhance the amount of fluorescence which becomes available for detection.

The exciting light is preferably pulsed. This gives several advantages. Thus, pulsing makes it possible to compensate for any background signal in the measurement. In some of the important types of measurements on fluids containing biological material, e.g., in purification plants, day-light may generate an error signal, which can be compensated for by subtracting the background signal from the peak fluorescence signal following excitation. Another important advantage of the use of pulsed induction of fluorescence is that also the fluorescence generated is measured as a pulsed signal, whereby the peak intensity may be orders of magnitude higher than when exciting the fluid medium with continuous light having the same mean intensity. Thus, when pulsing the output of the light source, the peak intensity of the light pulses may correspond to the intensity emitted from a continuous 50–100 kW light source.

When using a pulsed light source, care should be taken to shield the detecting electronics from noise generated by the light source and its controlling electronics. An advantageous way of reducing the noise due to the pulsed light source is to separate the pulsing and the detecting electronics physically. This may be accomplished by the use of fibre optics. Thus, in a preferred embodiment of the apparatus according to the invention, the light emitter is a light emitting end of a fibre optical means, such as an optical fibre bundle, having a light receiving end adapted to receive light from a light source.

The fact that an optical fibre emits light from a very small area and at a maximum angle determined by the fibre material and the wavelength of the light, the maximum angle being smaller for Ultra Violet-transmitting fibres than for fibres transmitting visual light, is compensated for by the fact that the light emitting end of the fibre optical means is positioned at a distance from the sensor face. As will be explained in greater detail in connection with the drawing, this configuration makes it possible for the fibre optical means to illuminate and thus excite a satisfactorily large area of a turbid medium.

It is believed that the special way of using fibre optics where the light emitting end thereof is kept at a distance from the sensor face, thus enlarging the area of illumination and at the same time permitting a detector to "see" all or a considerable proportion of the illuminated area is novel per se, and thus, a particular aspect of the present invention can be expressed as an apparatus for inducing and measuring fluorescence in a fluid medium containing at least one fluorophore, the apparatus comprising:

a light emitter adapted to emit light of a wavelength able to excite fluorophores in the fluid medium, optical fibre means adapted to receive and guide exciting light from the light emitter and having a light emitting end, a light detector adapted to detect fluorescence emitted by the fluorophores excited by the exciting light, a sensor body having a sensor face adapted to be exposed to the fluid medium, the sensor body being adapted to receive exciting light from the light emitting end of the optical fibre means, and to transmit the received exciting light into the fluid medium, to receive fluorescence emitted by excited fluorosphores in the fluid medium, and to transmit at least part of the received fluorescence to the light detector, the sensor face being positioned in a distance from the light emitting end of the optical fibre means, and the relative positioning of the light emitting end of the optical fibre means, the sensor face, and the optical detector being such that light emitted by the optical fibre means is able to illuminate a part of the sensor face, and such that the detector is able to receive light from at least a part of the thus illuminated part of the sensor face.

Depending on the particular measurement to be performed, the pulsing may be performed with time intervals varying from fractions of a second to the order of minutes or hours. The duration of each single pulse is normally of the order of fractions of a second.

Alternatively, in a preferred embodiment of the present invention, a measurement may be performed by transmitting a series of pulses, such as 12 to 200 pulses, measuring the generated fluorescence in the peaks and between the peaks and assigning the mean value of the measured fluorescence to be the actual value. The pulses in the measurement may in principle be generated at any frequency; at present, a frequency of in the order of 4 Hz is preferred. Measurements may be performed at regular intervals, such as 10 to 60 times or more an hour. Naturally the frequency of the pulses in the measurement, the number of pulses in the measurement and the time interval in which the measurements are performed is adapted to each other. If e.g. 180 measurements are performed an hour, the number of pulses used for each measurement is usually in the order of 4–32.

For the generation of the exciting light, a wide variety of light sources may be used, ranging from Ultra Violet sources to broad-band sources, depending on the properties of the fluorophores to be measured. For most applications, the exciting light will be light in the Ultra Violet region.

The wavelength range of the exciting light is normally limited, e.g., by incorporating, in the light emitter, light filtering means permitting the light emitter to emit filtered light. In a preferred embodiment, the filtering means is placed between the light source and the light receiving end of the fibre optics.

The sensor body is normally a monolithic body, but it is possible, and within the scope of the present invention, to establish the function of the sensor body by combination of two or more individual parts which together constitute the sensor body. The sensor body may be a hollow body, which may present the advantage that the amount of material in the light path which could potentially generate fluorescence (most materials are capable of some degree of fluorescence) is reduced, but for most practical purposes, it is preferred that the sensor body is solid. The use of a solid sensor body has the advantage that a compact and robust design can be obtained, and that the danger of formation of water of condensation at critical internal parts of the apparatus is obviated or considerably reduced.

The sensor body may be made of any material which is capable of effectively transmitting the exciting light and the fluorescence, such as quartz or sapphire when the exciting light is in the Ultra Violet region, or glass when the exciting light is in the visual range. Due to the exciting light travelling in the sensor body, fluorescence from the material constituting the sensor body may occur, depending on the material of the sensor body. Therefore, it is important to select a sensor body material which will emit as little fluorescence as possible. For most cases, this means that a high purity of the sensor body material should be secured, as impurities will tend to increase the amount of fluorescence.

It is preferred that the sensor body has a substantially symmetrical cross section in a direction transverse to the sensor face. In this connection, "transverse" should not be understood as limited to "perpendicular to", but rather includes both the perpendicular relationship and any slanted or oblique relationship. A suitable method of producing a sensor body of the kind disclosed herein is to cut a piece of a rod of the material in question, e.g. a quartz rod, and subjecting the piece to working and polishing so as to bring it into a desired shape and establish end faces suitable as sensor face and face receiving the detector and the light emitter, respectively.

The cross section of the sensor body may, e.g., be substantially elliptical, in particular substantially circular.

The reflective property of the wall parts of the sensor body are suitably obtained due to a coating of the wall parts. The coating may be any suitable coating resulting in the desired reflecting properties, such as a coating selected from dielectric coatings and metal coatings. The method of application of the coating will be adapted to the coating material and may comprise application from a liquid or from a vapour. In a presently preferred embodiment, the sensor body is coated with an external coating with aluminum applied by vapour deposition.

The sensor body will normally be an elongated body.

The dimensions of the sensor body may vary over a wide range. Normally, the sensor body will have a length in the range of 3–50 mm, preferably in the range of 5–50 mm, more preferably in the range of 10–25 mm, such as about 15 mm. The diameter is normally in the range of 2–40 mm, preferably in the range of 3–30 mm, more preferably in the range of 5–20 mm, such as about 10 mm.

The practical physical appearance of the apparatus according to the invention can be varied in many ways, depending on the environment in which the apparatus is to be used. As an example may be mentioned an embodiment wherein at least a portion of the sensor body is adapted to extend into the fluid; in this embodiment, the sensor face is less prone to become covered or fouled by, e.g. microorganisms or any material present in the fluid to be processed.

As will be understood from the above discussion, the light emitter may be, and often preferably is, the light emitting end of a fibre optical means, but it is also within the scope of the invention that a light source arranged in connection with the sensor body serves as the light emitter.

BRIEF DESCRIPTION OF THE DRAWINGS

The invention will now be described with reference to the drawing where.

DETAILED DESCRIPTION

Figure 1:
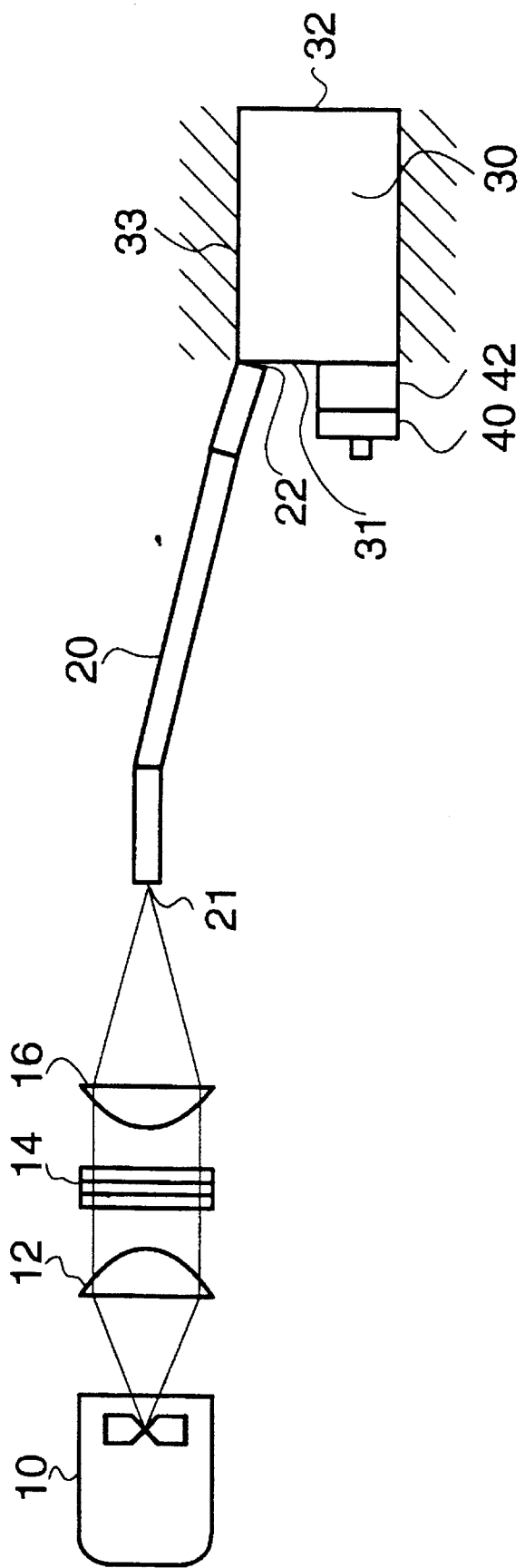
FIG. 1 is a schematic figure of a presently preferred embodiment of a sensor according to the invention.

In FIG. 1, light from an exciting light source 10, such as UV light from a flash lamp controlled by electronic controlling means (not shown), is collimated by a lens 12. From the collimated light, a band pass filter 14 removes substantially all light not having a wavelength able to excite the fluorophores in the fluid. After filtration, the light passes a lens 16 and is thereby focused onto a light receiving end 21 of a fibre optical means 20, preferably a fiber bundle known per se. The exciting light is then guided by the fibre optical means 20 to a light emitting end 22 of the fibre optical means 20 and from there to a solid sensor body 30 of a material which is capable of transmitting the exciting light and fluorescence generated as a result of excitation with the exciting light, such as quartz. In FIG. 1, the body is shaped as a circular cylinder having end parts 31 and 32 and a wall part 33 constituted by the outer cylindrical circumference and comprising a vapour-deposited aluminum coating of a thickness of a few μm, constituting a reflecting layer surrounding the sensor body 30. The exciting light then travels through the sensor body 30 to the end part 32 which constitutes the sensor face of the body adapted to be in contact with the fluid containing the fluorophores.

When the exciting light enters the sensor body 30, a major part thereof illuminates the sensor face 32, while a part of this light will be directed toward the wall part 33 of the sensor body 30. The part of the exciting light directed toward this wall part 33 will be reflected by the wall part 33 whereby the reflected light will be directed to the sensor face 32, thus minimizing light losses.

When the sensor face 32 is exposed to a fluid containing fluorophores excitable by the exciting light, fluorescence will be generated in the fluid when the exciting light enters the fluid. Part of this fluorescence will be directed toward the sensor face 32 and will enter the sensor body 30.

A light detector 40 is positioned in a position at the end part 31 where it can directly detect fluorescence from the major part of the sensor face 32. In addition, the detector 40 receives fluorescence reflected from the wall parts 33, whereby a larger amount of the fluorescence from the excited fluorophores is detected. Therefore, the reflecting wall parts 33 increase the sensitivity of the sensor.

The detector 40 transforms the light signal received into an electrical signal representative of the amount of light received. The electrical signal is conducted to recording and/or calculating and/or process-regulating electronics, not shown.

Figure 2:
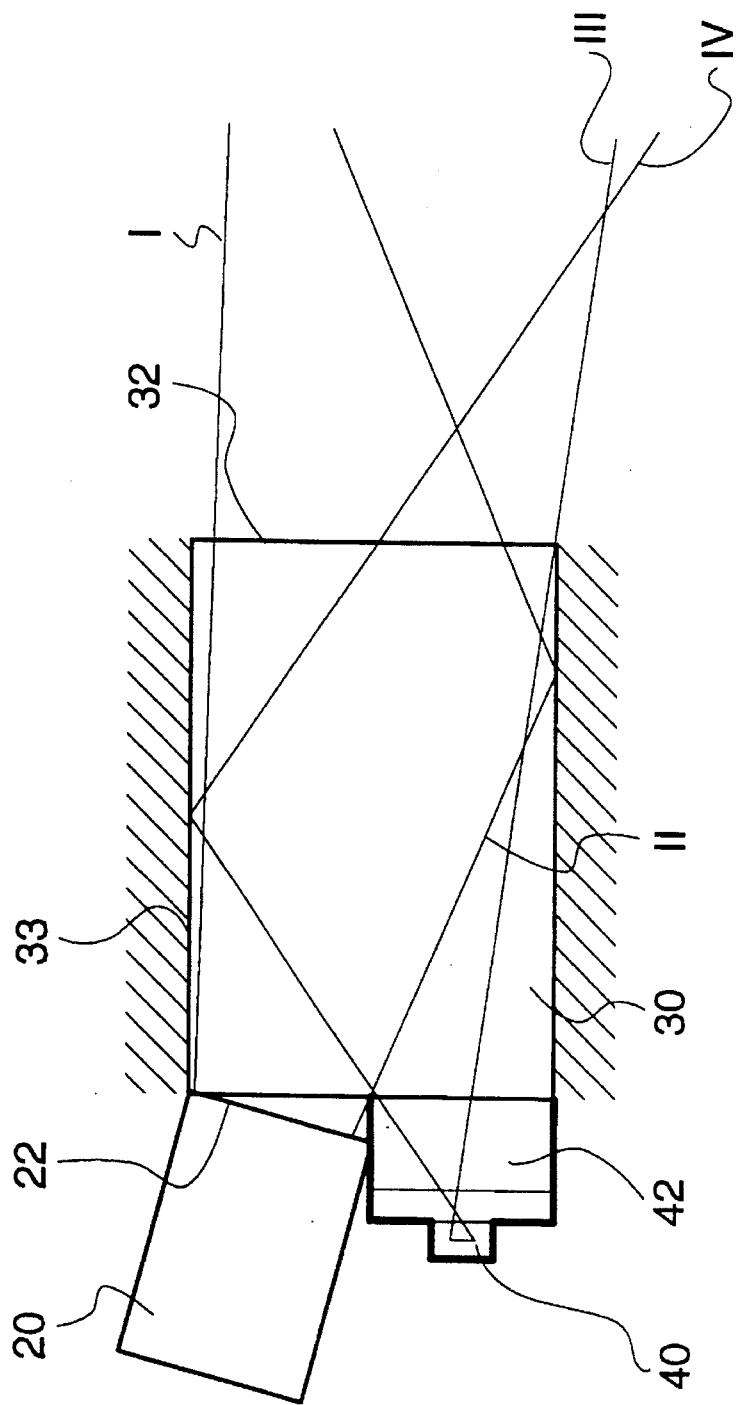
FIG. 2 is a detailed drawing of the operation of the sensor body.

When the fluid medium to which the sensor face 32 is exposed is a highly turbid medium, such as sewage or waste water treated with a mixed culture of microorganisms in a water purification plant, the exciting light will not travel more than a few mm into the medium before it is absorbed to a very considerable extent, and likewise, the fluorescence generated due to the excitation will not be detectable through a medium thickness of more than very few mm. For this reason, it is important, in order to obtain a realistic volume on which to perform the measurement, that the sensor face has a relative large area through which a reasonable volume of the medium can be exposed to the exciting light, and it is also important that the detector is able to receive the fluorescence from at least a portion of the area where the illumination takes place, preferably from a predominant portion of this area. FIG. 2 illustrates these considerations.

In FIG. 2, a light emitter in the form of a light emitting end 22 of a fibre optical means 20 is seen abutting the sensor body 30. As described further above, light emitted from fibre optical means is emitted having a maximum angle defined by the materials defining the core and the cladding of the individual fibres. Lines I and II illustrate this maximum angle for a preferred embodiment in which the fibre optical means 20 is a fibre optical bundle. It is seen that part of the emitted exciting light (e.g. II) is directed toward the wall parts 33 and, after a reflection on the wall parts 33, is directed toward the sensor face 32. It is seen that in this preferred embodiment, the predominant part of the sensor face 32 is illuminated directly by the exciting light. In this preferred embodiment, the fibre optical bundle 20 is positioned so as to primarily illuminate the part of the sensor face 32 which is closest to the detector 40.

Lines III and IV in FIG. 2 give examples of fluorescence generated by the fluorophores which either directly (III) or through a reflection on the wall parts 33 (IV) is directed to the sensitive surface 50 of the detector. It is evident that the reflection at the wall parts 33 considerably increases the amount of the fluorescence received by the detector 40.

EXAMPLE

As an example, a preferred embodiment of a sensor according to the present invention may comprise:

| | | |
|---|---|---|
| light emitter | 10 | bulb type xenon flash lamp |
| collimating lens | 12 | aspheric condenser lens |
| filter | 14 | UV band pass filter 300–400 nm |
| focusing lens | 16 | plano convex quartz lens |
| fiber optical bundle | 20 | quartz/quartz fibres, 3 mm diameter |
| sensor body | 30 | quartz cylinder |
| reflecting coating | | aluminum, vapour deposited |
| filter | 42 | visual band pass filter 400–500 nm |
| detector | 40 | PIN silicon diode |

The sensor body is preferably a solid quartz rod having dimensions:

diameter: 10 mm length: 15 mm.

Of course, the shape and size of the sensor body may be different. As the function of the body is solely to guide the light, any shape, size, and materials supporting this purpose may be used.

The exterior of the quartz body has preferably been polished whereafter the wall parts have been coated with a few μm of aluminum applied by vapour deposition.

The lenses are preferably selected so that the light focused onto an end of the fibre optical bundle has a shape and size substantially identical to those of the light emitting parts of the light source.

As the sensor body is polished, it is sufficient to position the light emitting end of the fibre optical bundle outside the sensor body, preferably in abutting relationship thereto as shown in FIG. 2, so that the exciting light, when exiting the fibre optical bundle, enters the sensor body and illuminates the sensor face as described above. It will be understood, however, that it is also possible—land may be preferred for some purposes to—design the sensor body in a shape which secures a better transfer of the light from the fibre optical bundle to the sensor body, such as, e.g., with a bore receiving the fibre optical bundle.

The light source of the sensor is preferably pulsed with a frequency of 4 Hz during the measurements. The detector then generates an electrical signal corresponding to the pulses of fluorescence generated by the fluorophores. Any signal corresponding to a background signal e.g. daylight, is measured between the fluorescence pulses. It is preferred that the individual peaks from the detected fluorescence peaks are converted to a mean value for the measurement. The background signal is also preferred to be a mean value of the detected background signal during the measurement.

For the detector to be able to precisely detect the fluorescence pulses, the sensitive area of the detector should preferably be relatively small, such as an area of about 5–10 $mm^2$, or smaller. In the above-mentioned presently preferred embodiment, the sensitive area of the detector is about 7 $mm^2$. The size of the sensitive area of the detector defines the speed of the detector. Pulses having a small duration in time should be detected by a detector having a small sensitive area.

Of course a smaller sensitive area is less sensitive than a larger sensitive area. However, this may be compensated for by strong pulses of the exciting light generating more fluorescence than if the light was continuous with the same mean intensity. Furthermore, a detector having a large sensitive area generates more noise than a detector having a small sensitive area.

This also has the advantage that detectors with small sensitive areas are usually cheaper than detectors having large sensitive areas. For this sensor, a small commercially available silicon PIN photodiode is suitable.

When combining the detector having a small sensitive area and the pulsed mode of the light source, an overall larger output signal may be obtained without reducing the signal to noise ratio below that obtained by using a sensor operating in continuous mode and using a detector having a larger sensitive area. The signal to noise ratio depends on both the noise generated by the sensitive area of the detector and the amplification of the signal.

When subtracting the background signal from the peak of the fluorescence pulse, the amount of fluorophores in the fluid may be evaluated or, if desired, calculated on the basis of suitable calibration in manners known per se.

COMPARISON EXPERIMENT

To illustrate the increased sensitivity of a sensor according to the present invention compared to the commercially available sensor, a test has been performed in the aeration tank of the Central Purification Plant in the city of Viborg, Denmark.

The aeration tank of the purification plant contains a mixed culture of microorganisms. The microorganisms in the mixed culture contain NADH which is a fluorophore. The amount of NADH in the microorganisms depend on the activity level of the organisms.

In the test, a sensor according to the present invention and corresponding to the preferred embodiment illustrated herein and described in the Example above was tested against a commercially available fluorescence sensor available from BioChem Technology Inc., Malvern, Pa., U.S.A.

The sensor according to the invention was operated with one measurement per minute, 200 pulses per measurement at 4 Hz.

The commercial sensor comprises a front part adapted to be exposed to a liquid environment in which a fluorophore is to be determined. The front part comprises a circular channel through which a light beam from a continuous lamp travels to and through a front window which is sealingly mounted at the front end of the channel. The channel is surrounded by an annular light detector positioned behind annular optical filters and positioned as close to the front end of the sensor as possible, taking the optical filters into account. Due to this design, the detector is not able to receive fluorescent light through the part of the window which transmits light from the light emitter, and the "field of view" of the detector therefore has a "blind spot" immediately in front of the window, as the field of view does not comprise any substantial part of the volume of the liquid environment which is immediately adjacent to the window.

Both sensors were tested during the same period of time, and they were placed in the same measuring site in the fluid. The test was performed over 16 hours.

FIGS. 3A and 3B shows the current output from the two detectors, measured in mA, as a function of time, measured in hours. FIG. 3A shows the output from a sensor according to the present invention, and FIG. 3B shows the output from the commercially available sensor.

Figure 3:
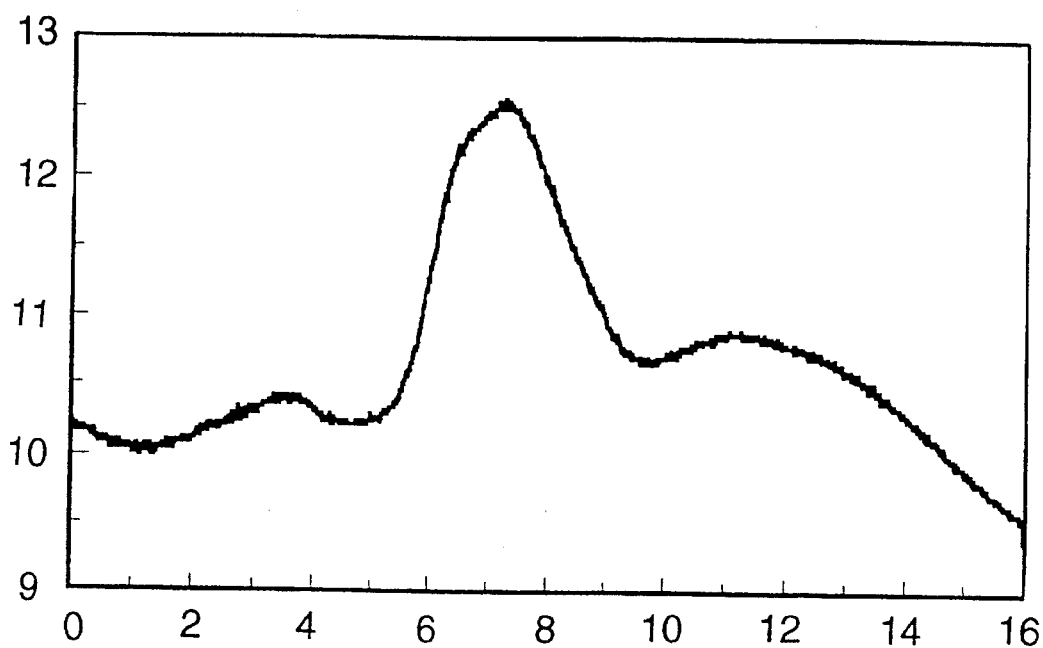
FIGS. 3A and 3B shows a test performed to illustrate the increased sensitivity of a sensor according to the present invention compared to a commercially available sensor.
Figure 3:
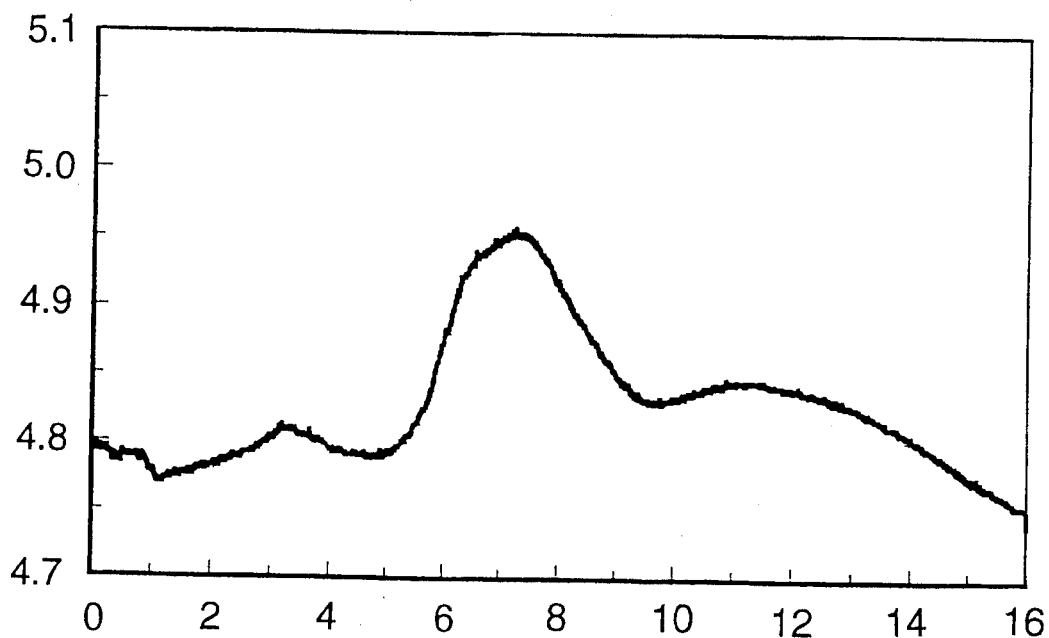

As is seen from FIG. 3, the output from the sensor according to the present invention is a factor 2.5 higher than that of the commercially available sensor. The higher output is generated by the sensor according to the invention operating in pulsing mode as the signal to noise ratio of this sensor makes this amplification possible.

But what is more important, the sensor according to the present invention has a dynamic range (the current difference between the highest and the lowest current in the measurement) of 3.2 mA, whereas the commercially available sensor has a dynamic range of only 0.2 mA From this, it is evident that the sensor according to the present invention is extremely useful for when performing exact and highly sensitive measurements for e.g. precisely monitoring a process in medium of high turbidity such as a purification plant.

Figure 4:
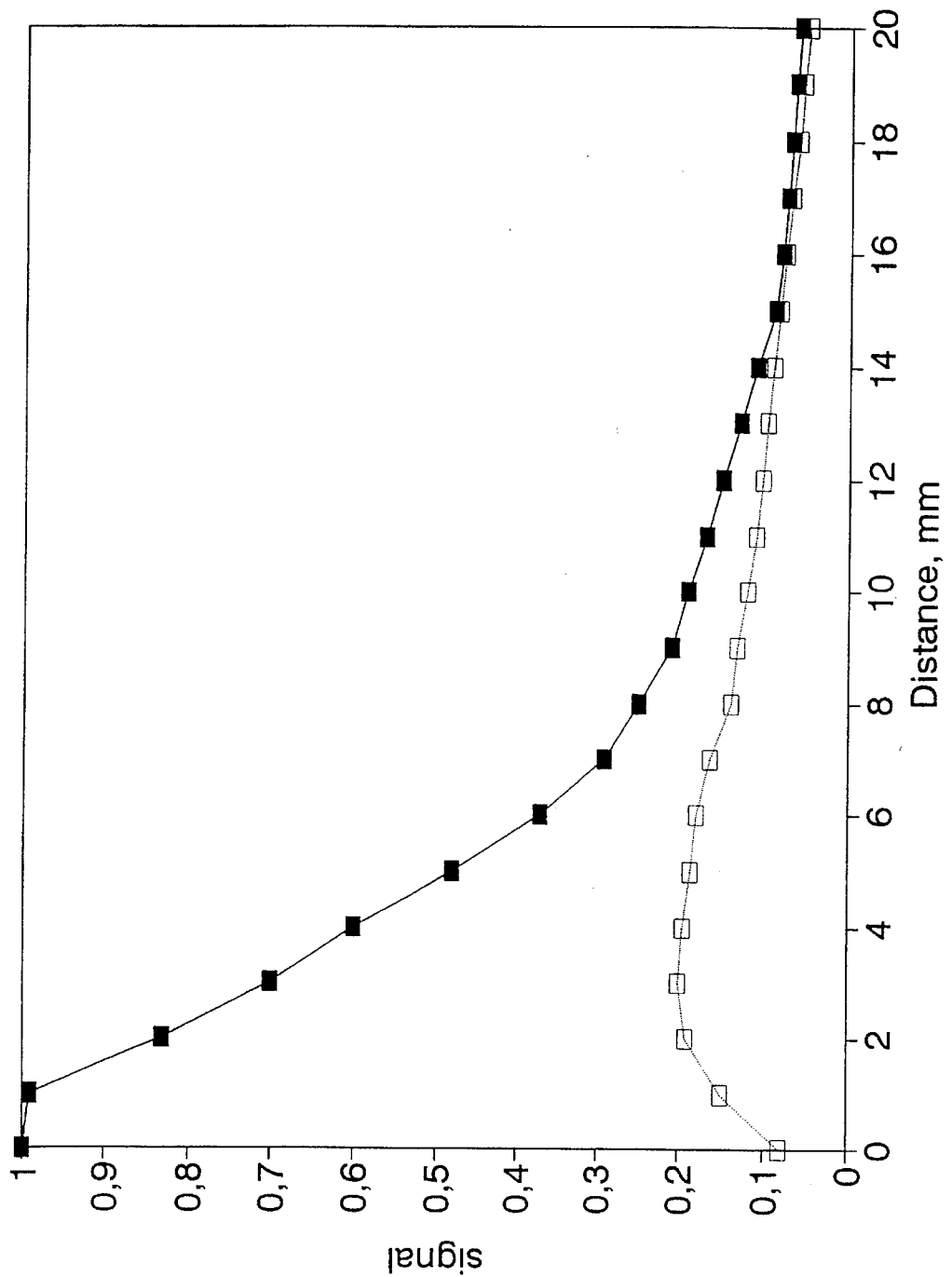
FIG. 4 illustrates a comparison of the sensitivity of the sensor according to the invention and the sensitivity of the commercially available sensor; the sensitivity is taken as the sensor output as a function of the distance from a fluorescent object to the end of the sensor.

FIG. 4 illustrates the sensitivity of the sensor according to the invention, operated in the same manner as above, compared to the commercially available sensor. The sensitivity was determined by positioning a fluorescent object, in the form of a piece of paper, in front of the sensors while measuring the sensor output as a function of the distance from the end of the sensor to the paper. The maximum output of the sensor according to the invention is regulated to 1; the output of the commercially available sensor is regulated in relation thereto.

From this figure, the consequence of the blind spot of the commercially available sensor is obvious: this sensor has maximum sensitivity when the fluorescing object is at a distance of 3 mm from the sensor. The sensor according to the invention has optimum sensitivity when the fluorescent medium is as close to the end of the sensor as possible.

In a turbid medium, such as in a waste water purification plant, light is almost totally attenuated after travelling only a few mm in the medium. Thus, the major part of the generated fluorescence is generated just in front of the front end of the sensor and, of course, in the area of the front end of the sensor in which the medium is illuminated: in the blind spot of the commercially available sensor. Thus, it is obvious that the optimum sensor for use in turbid media should have optimum sensitivity as close to the end of the sensor as possible as well as a large area in which fluorescence is generated and from which this fluorescence may be detected.

The optimum sensitivity of the commercially available sensor is 20% of that of the sensor according to the invention. This is again caused by the sensor according to the present invention offering a better signal due to the better signal to noise ratio offered by the use of pulsed mode operation and a more suitable structure of the sensor body; the reflecting coating on the sensor body also plays a role in increasing the sensitivity of the sensor according to the invention.

Even though the sensor according to the present invention, thus, possesses optimum features and sensitivity for use in the generation and detection of fluorescence in this type of medium, the sensor possesses the same features in less turbid media where the exciting light is launched a larger distance into the medium.

The sensor according to the invention offers the same degree of precise determinations in less turbid media as the overlap of the volume of the medium excited by the exciting light and the volume from which emitted fluorescence may be detected is large throughout the medium.

We claim:

1. An apparatus for inducing and detecting fluorescence in a fluid medium containing at least one fluorophore, the apparatus comprising:

a light emitter adapted to emit exciting light of a particular wavelength capable of exciting fluorophores in the fluid medium;

a light detector adapted to detect fluorescence emitted by the fluorophores excited by the exciting light; and a solid sensor body having internally reflecting wall parts capable of reflecting at least light having a wavelength corresponding to the particular wavelength and having a sensor face adapted to be exposed to the fluid medium, the sensor body being adapted to receive the exciting light from the light emitter, to transmit the received exciting light into the fluid medium through the sensor face, to receive, through the sensor face, fluorescence emitted by excited fluorophores in the fluid medium, and to transmit at least part of the received fluorescence to the light detector, the sensor body being made of a material which is capable of effectively transmitting the exciting light and the fluorescence, wherein both the light emitter and the detector are positioned at positions at an end of the sensor body a distance from the sensor face, relative positioning of the light emitter, the detector, and the sensor face being such that the detector is able to receive light transmitted from at least a portion of that part of the sensor face which receives light from the light emitter, and wherein the relative positioning of the light emitter, the sensor face and the optical detector is such that light emitted by the light emitter may directly illuminate the predominant part of the sensor face.

2. An apparatus according to claim 1 wherein the relative positioning of the light emitter, the sensor face, and the light detector is such that the detector is able to directly receive light from a predominant proportion of the illuminated part of the sensor face.

3. An apparatus according to claim 1, wherein the light emitter comprises a light emitting end of a fibre optical means having a light receiving end adapted to receive light from a light source.

4. An apparatus according to claim 1, wherein the light emitter is capable of emitting pulsed light.

5. An apparatus according to claim 1, wherein at least part of the light which the light emitter is capable of emitting is in the Ultra Violet region.

6. An apparatus according to claim 1, further comprising light filtering means permitting the light emitter to emit filtered light.

7. An apparatus according to claim 1, wherein the sensor body comprises a monolithic body.

8. An apparatus according to claim 1, wherein the sensor body has a substantially symmetrical cross section in a direction transverse to the sensor face.

9. An apparatus according to claim 8, wherein the cross section is substantially elliptical or substantially circular.

10. An apparatus according to claim 1, wherein the sensor body comprises an elongated body.

11. An apparatus according to claim 1, wherein the reflective property of the wall parts of the sensor body are due to a coating of the wall parts.

12. An apparatus according to claim 1, wherein the sensor body has a length in the range of 3–50 mm and a diameter of in the range of 2–40 mm.

13. An apparatus according to claim 1, further comprising filter means for filtering the fluorescence to be detected by the light detector so that substantially only light having a wavelength in the wavelength region of the fluorescence emitted from the excited fluorophores is received by the detector.

14. An apparatus according to claim 3, wherein the fibre optical means comprises an optical fibre bundle.

15. An apparatus according to claim 10, wherein the elongated body comprises an elongated body made of quartz.

16. An apparatus according to claim 11, wherein the coating of the wall parts is a coating selected from the group consisting of dielectric coatings and metal coatings.

17. An apparatus according to claim 16, wherein the metal coating is an aluminum coating.

18. An apparatus according to claim 12, wherein the sensor body has a length in the range of 5–50 mm.

19. An apparatus according to claim 18, wherein the sensor body has a length in the range of 10–25 mm.

20. An apparatus according to claim 19, wherein the sensor body has a length of about 15 mm.

21. An apparatus according to claim 12, wherein the sensor body has a diameter in the range of 3–30 mm.

22. An apparatus according to claim 21, wherein the sensor body has a diameter in the range of 5–20 mm.

23. An apparatus according to claim 22, wherein the sensor body has a diameter of about 10 mm.

24. A method for inducing and detecting fluorescence in a fluid medium containing at least one fluorophore, the method comprising the steps of:

transmitting light from a light emitter positioned at an end of a solid sensor body having internally reflecting wall parts capable of at least reflecting light having a wavelength corresponding to a wavelength of the fluorescence, the light being transmitted through the sensor body and through a sensor face thereof into the fluid medium, the light emitted by the light emitter directly illuminating a predominant part of the sensor face, at least part of the light being exciting light of the wavelength capable of exciting the fluorophores so as to induce the emission of fluorescence, the sensor body being made of a material which is capable of effectively transmitting the exciting light and the fluorescence; and receiving, through the sensor face, fluorescence emitted by the excited fluorophores in the fluid medium, and transmitting at least part of the received fluorescence through the sensor body to a light detector adapted to detect the fluorescence emitted by the fluorophores excited by the exciting light and positioned at a position at the end of the sensor body, wherein at least part of the fluorescence transmitted to the detector includes fluorescence received through a part of the sensor face from which light from the light emitter is emitted to the fluid medium.

25. A method according to claim 24, wherein the fluid medium comprises a turbid medium.

26. A method according to claim 25, wherein the turbid medium comprises waste water which is being biodegraded by a mixed culture of microorganisms, the microorganisms containing at least one biogenic fluorophore, the fluorescence of which is inducible by the exciting light and detectable by the light detector.

* * * * *

UNITED STATES PATENT AND TRADEMARK OFFICE
CERTIFICATE OF CORRECTION

PATENT NO. : 5,557,415

DATED : September 17, 1996

INVENTOR(S) : Nielsen et al.

It is certified that error appears in the above-identified patent and that said Letters Patent is hereby corrected as shown below:

Col. 7, line 63: "land" should read --and--

Col. 10, line 44, Claim 1: insert --,-- after the word "body"

Col. 7, line 64, "purposes to-design" should read --purposes-to design--.

Signed and Sealed this

Thirteenth Day of January, 1998

Attest:

*Attesting Officer*

BRUCE LEHMAN

*Commissioner of Patents and Trademarks*